(12) United States Patent
Misener (10) Patent No.: US 11,850,338 B2
(45) Date of Patent: Dec. 26, 2023

(54) OPTICAL TIP-TRACKING SYSTEMS AND METHODS THEREOF

(71) Applicant: Bard Access Systems, Inc., Salt Lake City, UT (US)

(72) Inventor: Anthony K. Misener, Bountiful, UT (US)

(73) Assignee: Bard Access Systems, Inc., Salt Lake City, UT (US)

(*) Notice: Subject to any disclaimer, the term of this patent is extended or adjusted under 35 U.S.C. 154(b) by 302 days.

(21) Appl. No.: 17/105,310

(22) Filed: Nov. 25, 2020

(65) Prior Publication Data

US 2021/0154440 A1 May 27, 2021

Related U.S. Application Data

(60) Provisional application No. 62/940,107, filed on Nov. 25, 2019.

(51) Int. Cl.
*A61B 34/20* (2016.01)
*A61M 25/09* (2006.01)

(52) U.S. Cl.
CPC ............. *A61M 25/09* (2013.01); *A61B 34/20* (2016.02); *A61B 2034/2055* (2016.02); *A61M 2025/09175* (2013.01)

(58) Field of Classification Search
CPC ... A61B 5/06; A61B 34/20; A61B 2034/2055; A61B 5/064; A61B 5/0059; A61M 2025/09175
See application file for complete search history.

(56) References Cited

U.S. PATENT DOCUMENTS

| 4,813,429 A | 3/1989 | Eshel et al. |
| 5,099,845 A | 3/1992 | Besz et al. |

(Continued)

FOREIGN PATENT DOCUMENTS

| DE | 102016109601 A1 | 11/2017 |
| EP | 2240111 A2 | 10/2010 |

(Continued)

OTHER PUBLICATIONS

PCT/US2020/062396 filed Nov. 25, 2020 International Search Report and Written Opinion dated Mar. 2, 2021.

(Continued)

*Primary Examiner* — Joseph M Santos Rodriguez
*Assistant Examiner* — Amal Aly Farag
(74) *Attorney, Agent, or Firm* — Rutan & Tucker LLP (57) ABSTRACT

An optical tip-tracking system is disclosed including a light-emitting stylet, a light detector, and a console configured to operably connect to the light-emitting stylet and the light detector. The light-emitting stylet is configured to be disposed in a lumen of a catheter. The light-emitting stylet includes a light source in a distal-end portion of the light-emitting stylet configured to emit light. The light detector is configured to be placed over a patient. The light detector includes a plurality of photodetectors configured to detect the light emitted from the light source. The console is configured to instantiate an optical tip-tracking process for optically tracking the distal-end portion of the light-emitting stylet while the light-emitting stylet is disposed in a vasculature of the patient, the light source is emitting light, the light detector is disposed over the light-emitting stylet, and the photodetectors are detecting the light emitted from the light source.

18 Claims, 7 Drawing Sheets

(56) References Cited

U.S. PATENT DOCUMENTS

| | | | |
|---|---|---|---|
| 5,163,935 A | 11/1992 | Black et al. |
| 5,207,672 A | 5/1993 | Roth et al. |
| 5,211,165 A | 5/1993 | Dumoulin et al. |
| 5,275,151 A | 1/1994 | Shockey et al. |
| 5,423,321 A | 6/1995 | Fontenot |
| 5,454,807 A | 10/1995 | Lennox et al. |
| 5,517,997 A | 5/1996 | Fontenot |
| 5,622,170 A | 4/1997 | Schulz |
| 5,740,808 A | 4/1998 | Panescu et al. |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,729,735 B1* | 6/2010 | Burchman ............ A61B 5/1459 |
| | | | 600/339 |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,360,630 B2 | 6/2016 | Jenner et al. |
| 9,560,954 B2 | 2/2017 | Jacobs et al. |
| 9,622,706 B2 | 4/2017 | Dick et al. |
| 9,678,275 B1 | 6/2017 | Griffin |
| 10,231,753 B2 | 3/2019 | Burnside et al. |
| 10,327,830 B2 | 6/2019 | Grant et al. |
| 10,349,890 B2 | 7/2019 | Misener et al. |
| 10,492,876 B2 | 12/2019 | Anastassiou et al. |
| 10,568,586 B2 | 2/2020 | Begin et al. |
| 10,631,718 B2 | 4/2020 | Petroff et al. |
| 10,992,078 B2 | 4/2021 | Thompson et al. |
| 11,123,047 B2 | 9/2021 | Jaffer et al. |
| 2002/0198457 A1 | 12/2002 | Tearney et al. |
| 2003/0092995 A1 | 5/2003 | Thompson |
| 2004/0242995 A1 | 12/2004 | Maschke |
| 2005/0033264 A1 | 2/2005 | Redinger |
| 2005/0261598 A1* | 11/2005 | Banet .................... A61B 5/1112 |
| | | | 600/513 |
| 2006/0013523 A1 | 1/2006 | Childers et al. |
| 2006/0036164 A1 | 2/2006 | Wilson et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0156019 A1 | 7/2007 | Larkin et al. |
| 2007/0201793 A1 | 8/2007 | Askins et al. |
| 2007/0287886 A1 | 12/2007 | Saadat |
| 2007/0299425 A1 | 12/2007 | Waner et al. |
| 2008/0039715 A1* | 2/2008 | Wilson .................... A61B 5/06 |
| | | | 600/424 |
| 2008/0082004 A1* | 4/2008 | Banet .................. A61B 5/6833 |
| | | | 600/485 |
| 2008/0172119 A1 | 7/2008 | Yamasaki et al. |
| 2008/0183128 A1 | 7/2008 | Morriss et al. |
| 2008/0285909 A1 | 11/2008 | Younge et al. |
| 2009/0062634 A1 | 3/2009 | Say et al. |
| 2009/0137952 A1 | 5/2009 | Ramamurthy et al. |
| 2009/0234328 A1 | 9/2009 | Cox et al. |
| 2009/0304582 A1 | 12/2009 | Rousso et al. |
| 2009/0314925 A1 | 12/2009 | Van Vorhis et al. |
| 2010/0016729 A1 | 1/2010 | Futrell |
| 2010/0030063 A1 | 2/2010 | Lee et al. |
| 2010/0114115 A1 | 5/2010 | Schlesinger et al. |
| 2010/0312095 A1 | 12/2010 | Jenkins et al. |
| 2011/0144481 A1 | 6/2011 | Feer et al. |
| 2011/0166442 A1 | 7/2011 | Sarvazyan |
| 2011/0172680 A1 | 7/2011 | Younge et al. |
| 2011/0245662 A1 | 10/2011 | Eggers et al. |
| 2011/0295108 A1 | 12/2011 | Cox et al. |
| 2011/0313280 A1* | 12/2011 | Govari ................. A61B 5/6885 |
| | | | 600/424 |
| 2012/0046562 A1 | 2/2012 | Powers et al. |
| 2012/0143029 A1* | 6/2012 | Silverstein ........... A61B 8/0891 |
| | | | 600/374 |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0028554 A1 | 1/2013 | Wong et al. |
| 2013/0096482 A1 | 4/2013 | Bertrand et al. |
| 2013/0104884 A1 | 5/2013 | Vazales et al. |
| 2013/0188855 A1 | 7/2013 | Desjardins et al. |
| 2013/0204124 A1 | 8/2013 | Duindam et al. |
| 2013/0211246 A1 | 8/2013 | Parasher |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0121468 A1 | 5/2014 | Eichenholz |
| 2014/0221829 A1 | 8/2014 | Maitland et al. |
| 2014/0275997 A1 | 9/2014 | Chopra et al. |
| 2015/0029511 A1 | 1/2015 | Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0209113 A1 | 7/2015 | Burkholz et al. |
| 2015/0209117 A1 | 7/2015 | Flexman et al. |
| 2015/0254526 A1 | 9/2015 | Denissen |
| 2015/0320977 A1* | 11/2015 | Vitullo .............. A61M 25/0606 |
| | | | 604/510 |
| 2016/0018602 A1 | 1/2016 | Govari et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0213432 A1 | 7/2016 | Flexman et al. |
| 2016/0354038 A1 | 12/2016 | Demirtas et al. |
| 2017/0020394 A1 | 1/2017 | Harrington |
| 2017/0079681 A1 | 3/2017 | Burnside et al. |
| 2017/0082806 A1 | 3/2017 | Van Der Mark et al. |

(56) References Cited

U.S. PATENT DOCUMENTS

| | | |
|---|---|---|
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0311901 A1 | 11/2017 | Zhao et al. |
| 2017/0319279 A1 | 11/2017 | Fish et al. |
| 2018/0095231 A1 | 4/2018 | Lowell et al. |
| 2018/0113038 A1 | 4/2018 | Janabi-Sharifi et al. |
| 2018/0140170 A1 | 5/2018 | Van Putten et al. |
| 2018/0235709 A1 | 8/2018 | Donhowe et al. |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0279909 A1 | 10/2018 | Noonan et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2019/0059743 A1 | 2/2019 | Ramachandran et al. |
| 2019/0110844 A1 | 4/2019 | Misener et al. |
| 2019/0231272 A1 | 8/2019 | Yamaji |
| 2019/0237902 A1 | 8/2019 | Thompson et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374130 A1 | 12/2019 | Bydlon et al. |
| 2020/0046434 A1 | 2/2020 | Graetzel et al. |
| 2020/0054399 A1 | 2/2020 | Duindam et al. |
| 2020/0305983 A1 | 10/2020 | Yampolsky et al. |
| 2021/0045814 A1 | 2/2021 | Thompson et al. |
| 2021/0068911 A1 | 3/2021 | Walker et al. |
| 2021/0298680 A1 | 3/2021 | Sowards et al. |
| 2021/0244311 A1 | 8/2021 | Zhao et al. |
| 2021/0268229 A1 | 9/2021 | Sowards et al. |
| 2021/0271035 A1 | 9/2021 | Sowards et al. |
| 2021/0275257 A1 | 9/2021 | Prior et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0011192 A1 | 1/2022 | Misener et al. |
| 2022/0034733 A1 | 2/2022 | Misener et al. |
| 2022/0110695 A1 | 4/2022 | Sowards et al. |
| 2022/0152349 A1 | 5/2022 | Sowards et al. |
| 2022/0160209 A1 | 5/2022 | Sowards et al. |
| 2022/0211442 A1 | 7/2022 | McLaughlin et al. |
| 2022/0233246 A1 | 7/2022 | Misener et al. |
| 2022/0369934 A1 | 11/2022 | Sowards et al. |
| 2023/0081198 A1 | 3/2023 | Sowards et al. |
| 2023/0097431 A1 | 3/2023 | Sowards et al. |
| 2023/0101030 A1 | 3/2023 | Misener et al. |
| 2023/0108604 A1 | 4/2023 | Messerly et al. |
| 2023/0126813 A1 | 4/2023 | Sowards et al. |
| 2023/0243715 A1 | 8/2023 | Misener et al. |
| 2023/0248444 A1 | 8/2023 | Misener et al. |
| 2023/0251150 A1 | 8/2023 | Misener et al. |

FOREIGN PATENT DOCUMENTS

| | | |
|---|---|---|
| EP | 3545849 A1 | 10/2019 |
| EP | 3705020 A1 | 9/2020 |
| KR | 20190098512 A | 8/2019 |
| WO | 99/64099 A1 | 12/1999 |
| WO | 1999064099 A1 | 12/1999 |
| WO | 2006122001 A2 | 11/2006 |
| WO | 2009/155325 A2 | 12/2009 |
| WO | 2011121516 A2 | 10/2011 |
| WO | 2011141830 A1 | 11/2011 |
| WO | 2011150376 A1 | 12/2011 |
| WO | 2012064769 A2 | 5/2012 |
| WO | 2015074045 A2 | 5/2015 |
| WO | 2016038492 A1 | 3/2016 |
| WO | 2016/061431 A1 | 4/2016 |
| WO | 2016051302 A1 | 4/2016 |
| WO | 2018/096491 A1 | 5/2018 |
| WO | 2019037071 A1 | 2/2019 |
| WO | 2019/046769 A1 | 3/2019 |
| WO | 2019070423 A1 | 4/2019 |
| WO | 2019230713 A1 | 12/2019 |
| WO | 2020/182997 A1 | 9/2020 |
| WO | 2021030092 A1 | 2/2021 |
| WO | 2021108688 A1 | 6/2021 |
| WO | 2021108697 A1 | 6/2021 |
| WO | 2021/138096 A1 | 7/2021 |
| WO | 2022/031613 A1 | 2/2022 |
| WO | 2022/081723 A1 | 4/2022 |
| WO | 2022150411 A1 | 7/2022 |
| WO | 2022/164902 A1 | 8/2022 |
| WO | 2022/245987 A1 | 11/2022 |
| WO | 2023043954 A1 | 3/2023 |
| WO | 2023049443 A1 | 3/2023 |
| WO | 2023/055810 A1 | 4/2023 |
| WO | 2023/076143 A1 | 5/2023 |

OTHER PUBLICATIONS

PCT/US2020/062407 filed Nov. 25, 2020 International Search Report and Written Opinion dated Mar. 11, 2021.

PCT/US2020/062396 filed Nov. 25, 2020 International Preliminary Report on Patentability dated Jan. 29, 2021.

PCT/US2020/062407 filed Nov. 25, 2020 International Preliminary Report on Patentability dated Jan. 25, 2021.

PCT/US2022/011347 filed Jan. 5, 2022 International Search Report and Written Opinion dated May 3, 2022.

PCT/US2022/013897 filed Jan. 26, 2022 International Search Report and Written Opinion dated May 11, 2022.

U.S. Appl. No. 17/371,993, filed Jul. 9, 2021 Non-Final Office Action dated Jul. 12, 2022.

PCT/US2021/054802 filed Oct. 13, 2021 International Search Report and Written Opinion dated Feb. 2, 2022.

PCT/US2021/060849 filed Nov. 24, 2021 International Search Report and Written Opinion dated Mar. 9, 2022.

U.S. Appl. No. 15/947,267, filed Apr. 6, 2018 Final Office Action dated Apr. 22, 2022.

U.S. Appl. No. 17/185,777, filed Feb. 25, 2021 Non-Final Office Action dated Feb. 9, 2022.

PCT/US2018/026493 filed Apr. 6, 2018 International Search Report and Written Opinion dated Jun. 22, 2018.

PCT/US2020/044801 filed Aug. 3, 2020 International Search Report and Written Opinion dated Oct. 26, 2020.

PCT/US2021/019713 filed Feb. 25, 2021 International Search Report and Written Opinion dated Jul. 6, 2021.

PCT/US2021/020079 filed Feb. 26, 2021 International Search Report and Written Opinion dated Jun. 4, 2021.

U.S. Appl. No. 15/947,267, filed Apr. 6, 2018 Final Office Action dated Jun. 30, 2021.

U.S. Appl. No. 15/947,267, filed Apr. 6, 2018 Final Office Action dated Nov. 10, 2020.

U.S. Appl. No. 15/947,267, filed Apr. 6, 2018 Non-Final Office Action dated Mar. 12, 2021.

U.S. Appl. No. 15/947,267, filed Apr. 6, 2018 Non-Final Office Action dated May 29, 2020.

U.S. Appl. No. 15/947,267, filed Apr. 6, 2018 Non-Final Office Action dated Oct. 13, 2021.

PCT/US2022/029894 filed May 18, 2022, International Search Report and Written Opinion dated Sep. 1, 2022.

U.S. Appl. No. 17/105,259, filed Nov. 25, 2020, Notice of Allowance dated Jul. 20, 2022.

U.S. Appl. No. 17/357,561, filed Jun. 24, 2021 Non-Final Office Action dated Aug. 11, 2022.

U.S. Appl. No. 17/392,002, filed Aug. 2, 2021, Non-Final Office Action dated Sep. 12, 2022.

PCT/US2021/020732 filed Mar. 3, 2021 International Search Report and Written Opinion dated Jul. 5, 2021.

PCT/US2021/038899 filed Jun. 24, 2021 International Search Report and Written Opinion dated Oct. 6, 2021.

(56) References Cited

OTHER PUBLICATIONS

PCT/US2021/038954 filed Jun. 24, 2021 International Search Report and Written Opinion dated Oct. 28, 2021.
PCT/US2021/041128 filed Jul. 9, 2021 International Search Report and Written Opinion dated Oct. 25, 2021.
PCT/US2021/044216 filed Aug. 2, 2021 International Search Report and Written Opinion dated Nov. 18, 2021.
Jackle Sonja et al. "Three dimensional guidance including shape sensing of a stentgraft system for endovascular aneurysm repair." International Journal of Computer Assisted Radiology and Surgery, Springer DE. vol. 15, No. 6, May 7, 2020.
PCT/US2022/043706 filed Sep. 16, 2022 International Search Report and Written Opinion dated Nov. 24, 2022.
PCT/US2022/044696 filed Sep. 26, 2022 International Search Report and Written Opinion dated Jan. 23, 2023.
PCT/US2022/045051 filed Sep. 28, 2022 International Search Report and Written Opinion dated Jan. 2, 2023.
PCT/US2022/047538 filed Oct. 24, 2022 International Search Report and Written Opinion dated Jan. 26, 2023.
U.S. Appl. No. 15/947,267, filed Apr. 6, 2018 Examiner's Answer dated Novemeber 28, 2022.
U.S. Appl. No. 17/357,561, filed Jun. 24, 2021 Notice of Allowance dated Dec. 9, 2022.
U.S. Appl. No. 17/371,993, filed Jul. 9, 2021 Notice of Allowance dated Nov. 3, 2022.
U.S. Appl. No. 17/392,002, filed Aug. 2, 2021, Notice of Allowance dated Jan. 19, 2023.
Fiber Optic RealShape (FORS) technology—research. Philips. (Oct. 18, 2018). Retrieved Feb. 28, 2023, from https:// www.philips.com/a-w/research/research-programs/fors.html (Year: 2018).
U.S. Appl. No. 16/984,104, filed Aug. 3, 2020 Restriction Requirement dated Mar. 13, 2023.
U.S. Appl. No. 17/357,186, filed Jun. 24, 2021 Restriction Requirement dated Mar. 7, 2023.
U.S. Appl. No. 17/392,002, filed Aug. 2, 2021, Corrected Notice of Allowability dated Feb. 23, 2023.
U.S. Appl. No. 17/500,678, filed Oct. 13, 2021 Non-Final Office Action dated Mar. 15, 2023.
EP 20853352.1 filed Mar. 7, 2022 Extended European Search Report dated Jul. 27, 2023.
PCT/US2023/019239 filed Apr. 20, 2023 International Search Report and Written Opinion dated Jul. 20, 2023.
U.S. Appl. No. 16/984,104, filed Aug. 3, 2020 Non-Final Office Action dated Jun. 22, 2023.
U.S. Appl. No. 17/357,186, filed Jun. 24, 2021 Non Final Office Action dated May 30, 2023.

* cited by examiner

OPTICAL TIP-TRACKING SYSTEMS AND METHODS THEREOF

PRIORITY

This application claims the benefit of priority to U.S. Patent Application No. 62/940,107 filed Nov. 25, 2019, which is incorporated by reference in its entirety into this application.

BACKGROUND

Intravascular guidance of medical devices such as guidewires and catheters typically requires fluoroscopic methods for tracking tips of the medical devices and determining whether the tips are appropriately localized in their target anatomical structures. Such fluoroscopic methods expose clinicians and patients alike to harmful X-ray radiation. In some cases, the patients are exposed to potentially harmful contrast media needed for the fluoroscopic methods. Magnetic and electromagnetic means for tracking the tips of the medical devices obviate some of the foregoing issues with respect to exposure to radiation and potentially harmful contrast media, but the magnetic and electromagnetic means for tracking the tips of the medical devices are prone to interference.

Disclosed herein are optical tip-tracking systems and methods thereof that address the foregoing.

SUMMARY

Disclosed herein is an optical tip-tracking system including, in some embodiments, a light-emitting stylet, a light detector, and a console configured to operably connect to the light-emitting stylet and the light detector. The light-emitting stylet is configured to be disposed in a lumen of a catheter. The light-emitting stylet includes a light source in a distal-end portion of the light-emitting stylet configured to emit light. The light detector is configured to be placed over a patient. The light detector includes a plurality of photodetectors configured to detect the light emitted from the light source. The console includes memory and a processor configured to instantiate an optical tip-tracking process for optically tracking the distal-end portion of the light-emitting stylet while the light-emitting stylet is disposed in a vasculature of the patient, the light source is emitting light, the light detector is disposed over the light-emitting stylet, and the photodetectors are detecting the light emitted from the light source.

In some embodiments, the light source is a light-emitting diode ("LED").

In some embodiments, the light emitted from the light source has a center wavelength between about 650 nm to 1350 nm.

In some embodiments, the light emitted from the light source has a center wavelength between about 650 nm to 950 nm.

In some embodiments, the distal-end portion of the light-emitting stylet is configured to directionally emit light in one or more chosen directions.

In some embodiments, the light detector includes a housing having a patient-facing portion of the housing configured to transmit at least a portion of the light emitted from the light source to the photodetectors.

In some embodiments, the housing has a light-blocking portion of the housing opposite the patient-facing portion configured to block ambient light from the photodetectors.

In some embodiments, the photodetectors are arranged in an array such that the light emitted from the light source remains detectable by at least one photodetector of the photodetectors even when the light emitted from the light source is anatomically blocked from another one or more photodetectors of the photodetectors.

In some embodiments, the optical tip-tracking process is configured to provide tracking information as input to a display server of the console for optically tracking the distal-end portion of the light-emitting stylet in a graphical user interface on a display.

In some embodiments, the light-emitting stylet is configured to directly connect to the console.

In some embodiments, the light-emitting stylet is configured to indirectly connect to the console through an intervening multi-use cable.

In some embodiments, the light-emitting stylet is configured to indirectly connect to the console through the light detector.

In some embodiments, the light detector is configured to be placed over the patient and under a sterile drape. The light-emitting stylet includes a drape-piercing connector having a piercing element configured to pierce the sterile drape and insert into a receptacle of a light-detector connector extending from the light detector under the drape.

Also disclosed herein is an optical tip-tracking system including, in some embodiments, a catheter, a light-emitting stylet for the catheter, a light detector, and a console configured to operably connect to the light-emitting stylet and the light detector. The catheter includes a lumen extending through the catheter. The light-emitting stylet is configured to be disposed in a lumen of a catheter. The light-emitting stylet includes a light-emitting diode ("LED") in a distal-end portion of the light-emitting stylet configured to emit light having a center wavelength between about 650 nm to 1350 nm. The light detector is configured to be placed over a patient. The light detector includes a plurality of photodetectors configured to detect the light emitted from the LED. The console includes memory and a processor configured to instantiate an optical tip-tracking process for optically tracking the distal-end portion of the light-emitting stylet in a graphical user interface on a display while the light-emitting stylet is disposed in a vasculature of the patient, the LED is emitting light, the light detector is disposed over the light-emitting stylet, and the photodetectors are detecting the light emitted from the LED.

In some embodiments, the light detector is configured to be placed over the patient and under a sterile drape. The light-emitting stylet includes a drape-piercing connector configured to pierce the sterile drape and connect with a light-detector connector extending from the light detector under the drape.

Also disclosed herein is an optical tip-tracking system including, in some embodiments, a light-emitting stylet, a light detector, and a console configured to operably connect to the light-emitting stylet and the light detector. The light-emitting stylet is configured to be disposed in a lumen of a catheter. The light-emitting stylet includes an optical fiber configured to convey light to a distal-end portion of the light-emitting stylet for emitting light therefrom. The light detector is configured to be placed over a patient. The light detector includes a plurality of photodetectors configured to detect the light emitted from the light source. The console includes a light source for the light emitting stylet and memory and a processor. The memory and the processor are configured to instantiate an optical tip-tracking process for optically tracking the distal-end portion of the light-emitting stylet while the light-emitting stylet is disposed in a vasculature of the patient, the light source is emitting light, the light detector is disposed over the light-emitting stylet, and the photodetectors are detecting the light emitted from the light source.

Also disclosed herein is a method of an optical tip-tracking system including, in some embodiments, a disposing step of disposing a light-emitting stylet of the optical tip-tracking system in a lumen of a catheter. The light-emitting stylet includes a light source in a distal-end portion of the light-emitting stylet. The method also includes a placing step of placing a light detector of the optical tip-tracking system over a patient. The light detector includes a plurality of photodetectors. The method also includes an advancing step of advancing the catheter from an insertion site to a destination within a vasculature of the patient while emitting light from the light source and detecting the light with the photodetectors. The method also includes a viewing step of viewing a display screen of the optical tip-tracking system while the display screen graphically tracks the distal-end portion of the light-emitting stylet through the vasculature of the patient.

In some embodiments, the light source of the light-emitting stylet distally extends beyond a distal end of the catheter while advancing the catheter, thereby enabling the photodetectors of the light detector to detect the light emitted from the light source.

In some embodiments, the method also includes a placing step of placing a sterile drape over both the patient and the light detector. The method also includes a connecting step of connecting a drape-piercing connector of the light-emitting stylet with a light-detector connector extending from the light detector. The connecting step includes piercing the sterile drape with a piercing element of the drape-piercing connector before inserting the piercing element into a receptacle of the light-detector connector.

In some embodiments, the catheter is a central venous catheter ("CVC"). The advancing step includes advancing the CVC with the light-emitting stylet disposed therein through a right internal jugular vein, a right brachiocephalic vein, and into a superior vena cava ("SVC").

In some embodiments, the catheter is a peripherally inserted central catheter ("PICC"). The advancing step includes advancing the PICC with the light-emitting stylet disposed therein through a right basilic vein, a right axillary vein, a right subclavian vein, a right brachiocephalic vein, and into an SVC.

In some embodiments, the method also includes a ceasing step of ceasing to advance the catheter through the vasculature of the patient after determining the distal-end portion of light-emitting stylet is located at the destination by way of the display screen.

These and other features of the concepts provided herein will become more apparent to those of skill in the art in view of the accompanying drawings and following description, which describe particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Again, fluoroscopic methods typically used for tracking tips of medical devices such as guidewires and catheters expose clinicians and patients alike to harmful X-ray radiation. Magnetic and electromagnetic means for tracking the tips of the medical devices obviate some of the foregoing issues with respect to exposure to radiation, but the magnetic and electromagnetic means for tracking the tips of the medical devices are prone to interference.

Disclosed herein are optical tip-tracking systems and methods thereof that address the foregoing.

Optical Tip-Tracking Systems

Figure 1:
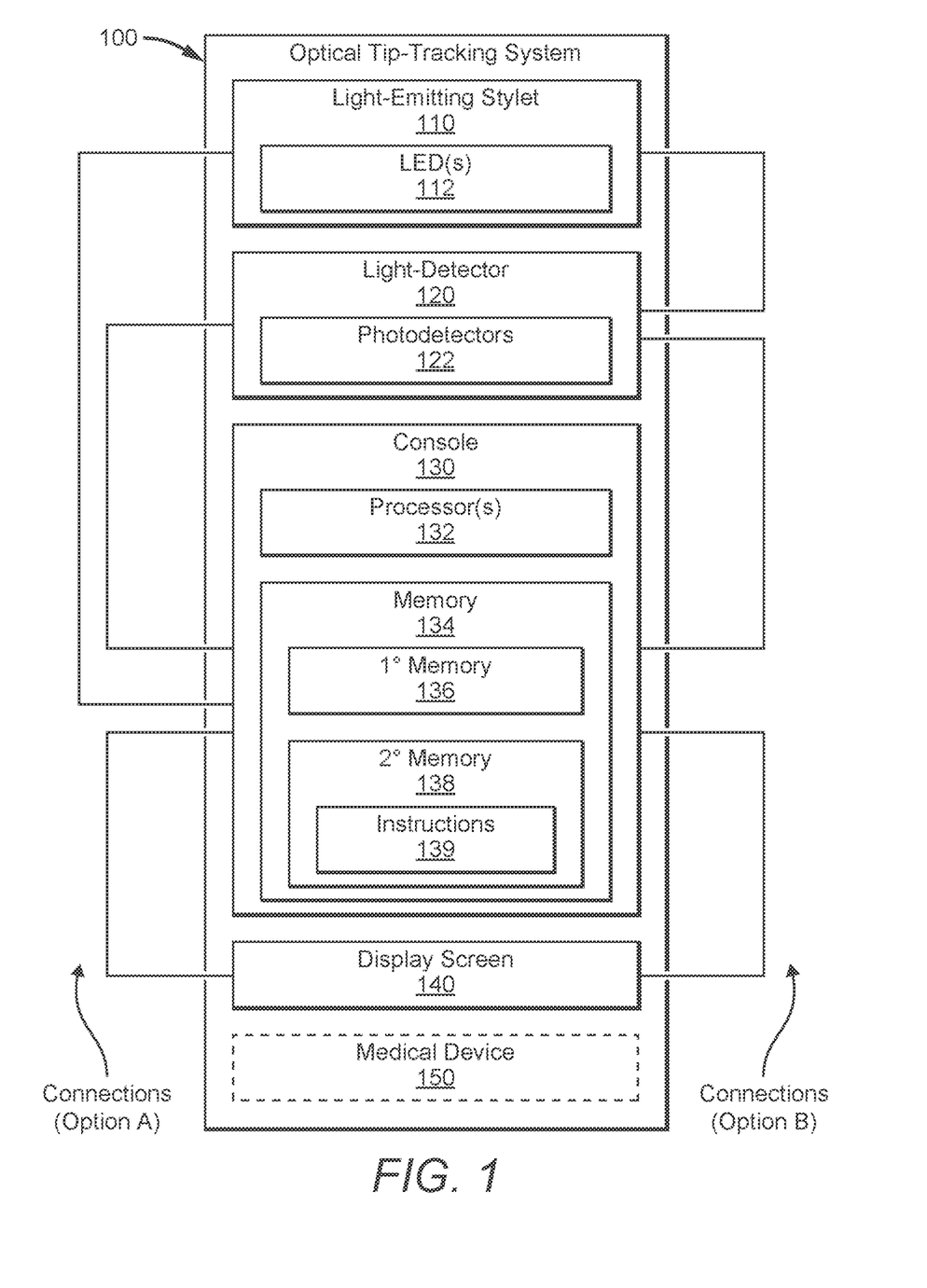
FIG. 1 provides a block diagram of a first optical tip-tracking system in accordance with some embodiments.
Figure 2:
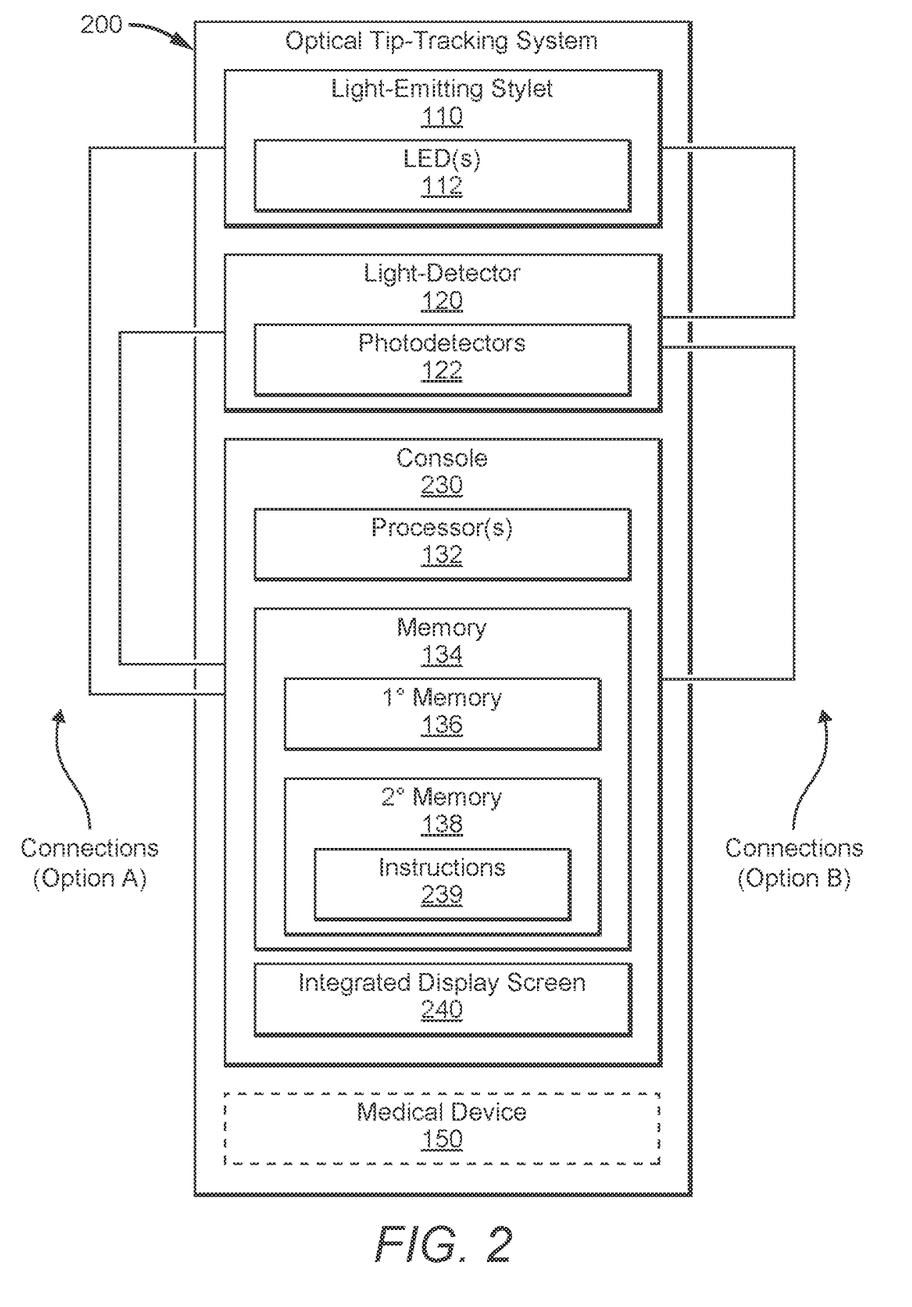
FIG. 2 provides a block diagram of a second optical tip-tracking system in accordance with some embodiments.
Figure 3:
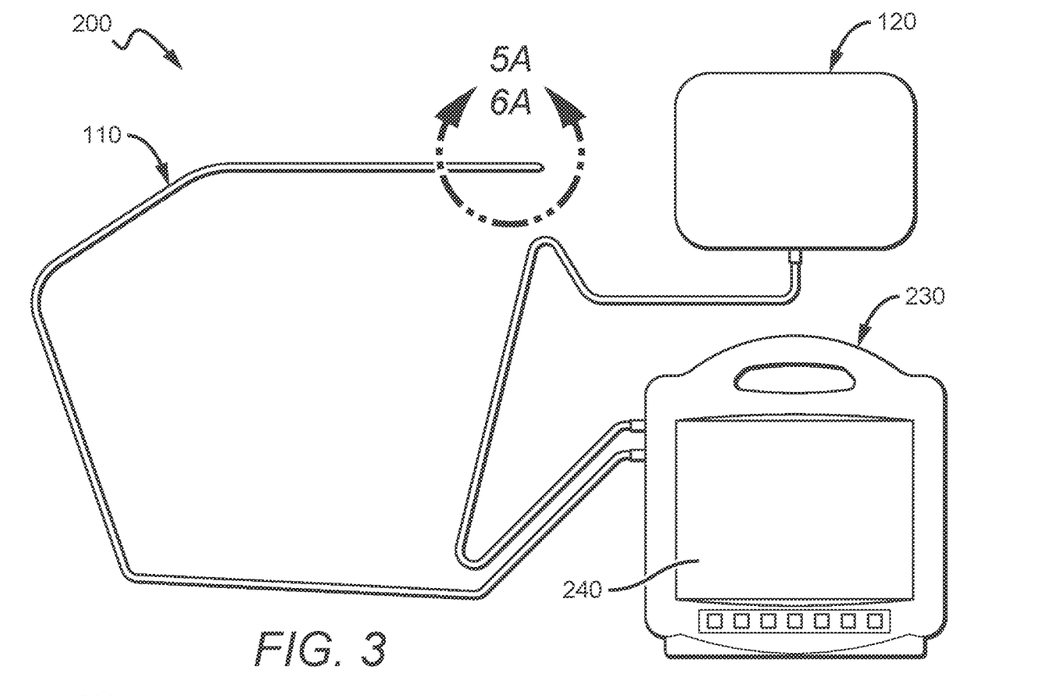
FIG. 3 illustrates the first optical tip-tracking system in accordance with some embodiments.
Figure 4:
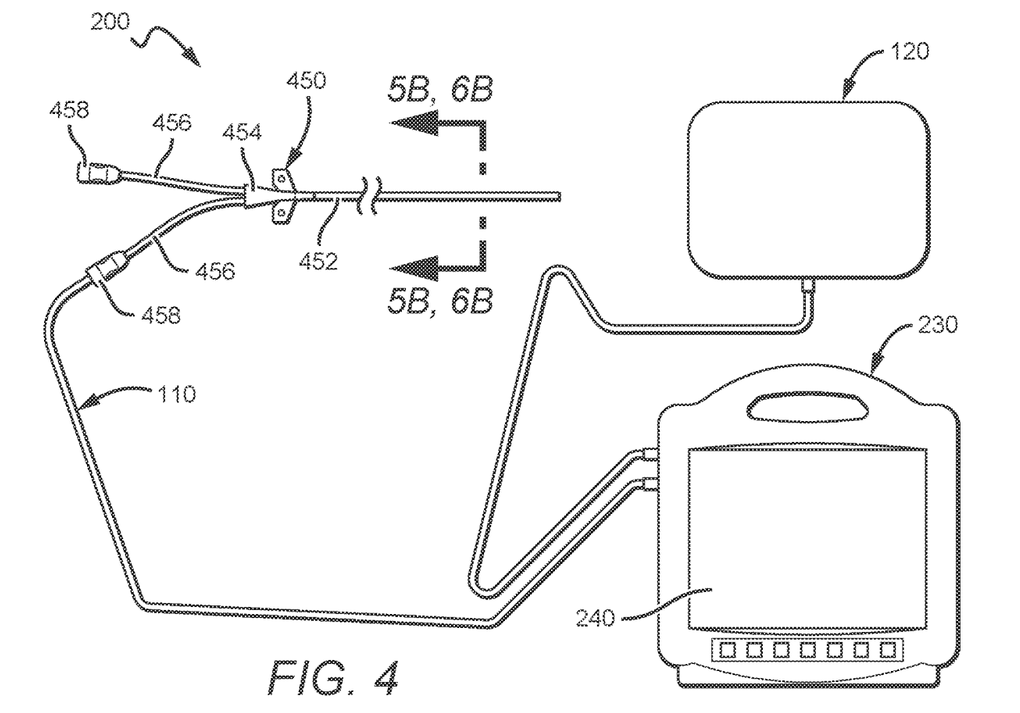
FIG. 4 illustrates the first optical tip-tracking system including a catheter in accordance with some embodiments.
Figure 8:
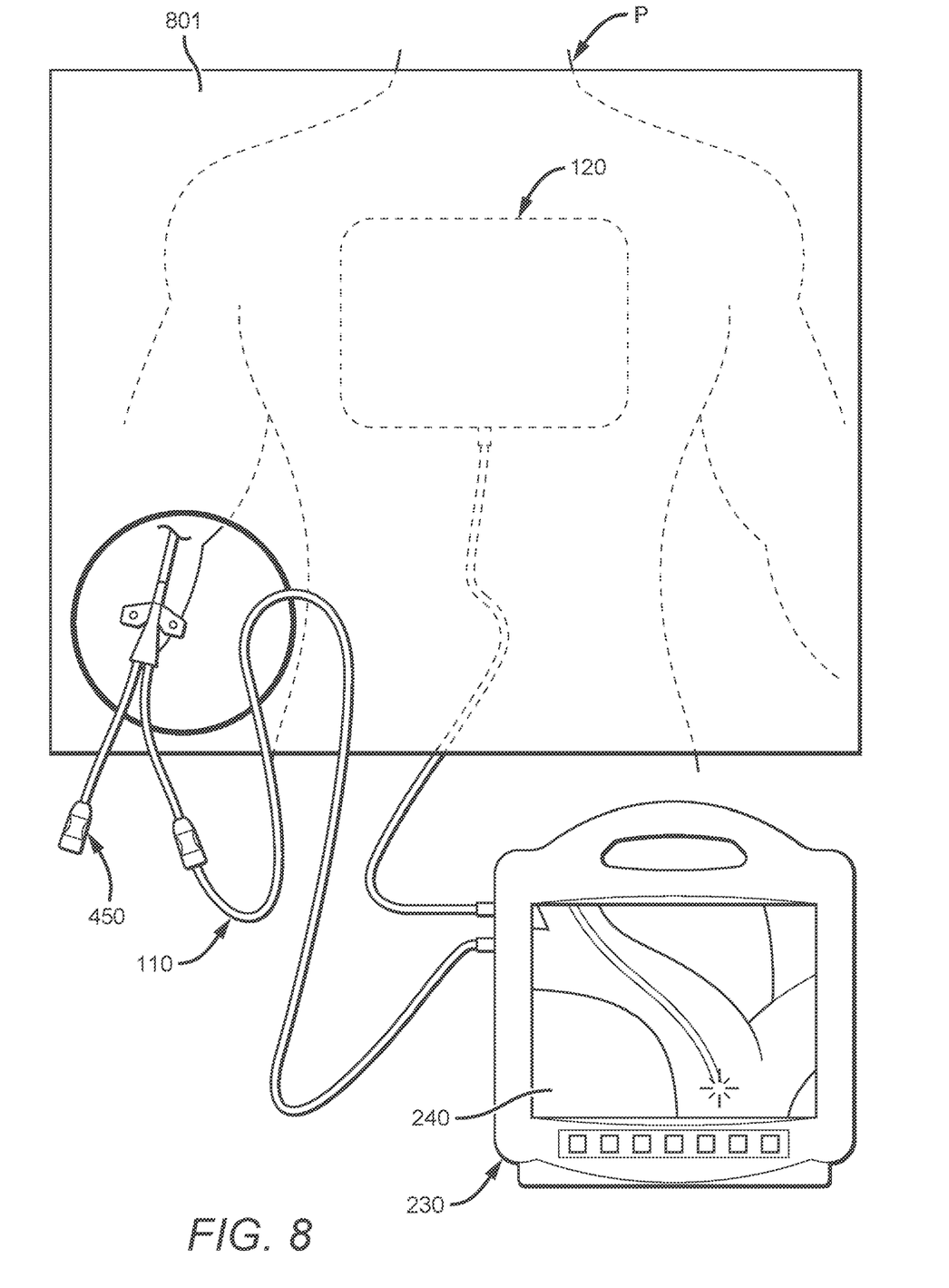
FIG. 8 illustrate the first optical tip-tracking system in use in accordance with some embodiments.
Figure 9:
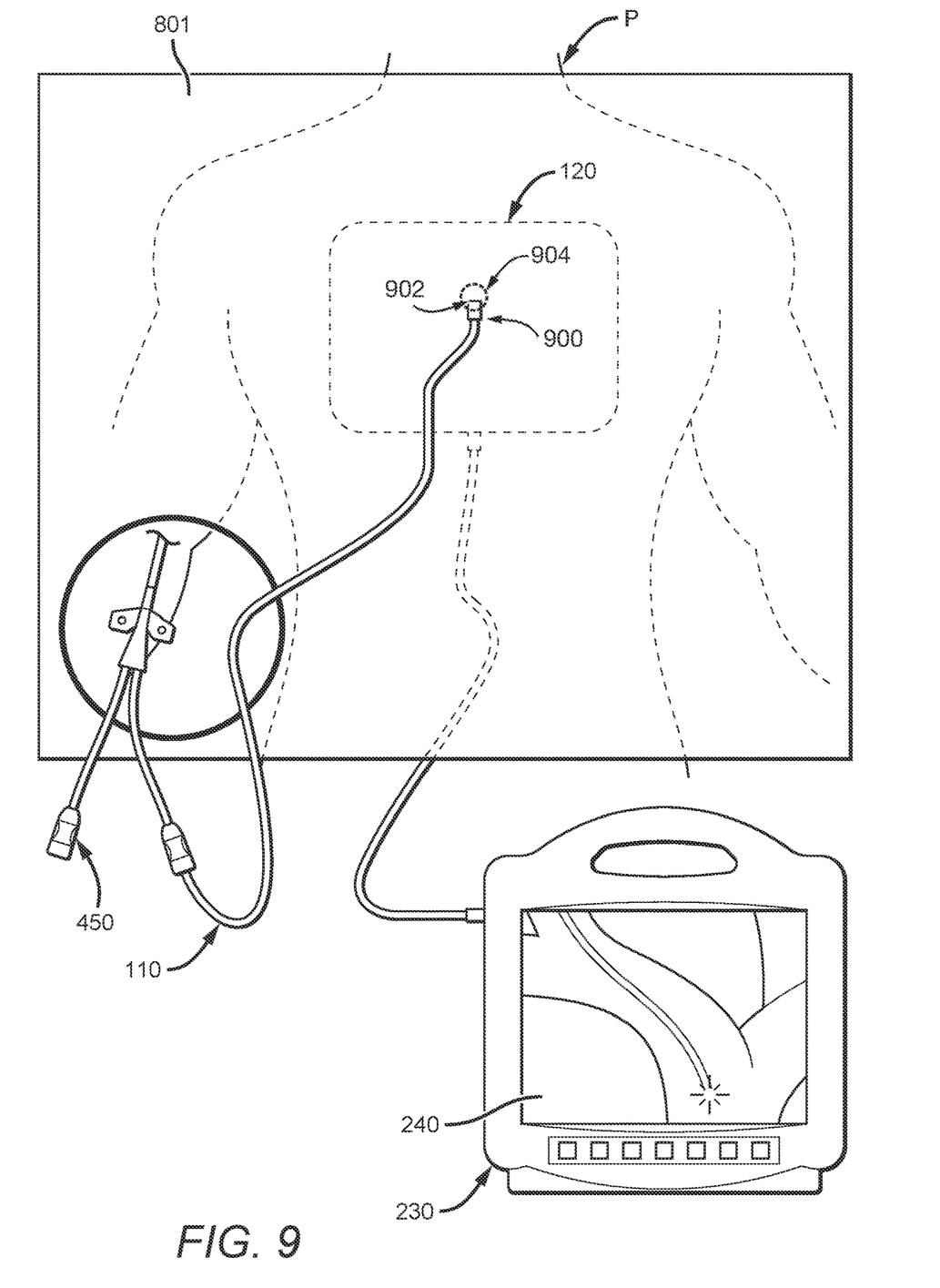
FIG. 9 illustrate the second optical tip-tracking system in use in accordance with some embodiments.

FIG. 1 provides a block diagram of a first optical tip-tracking system 100, FIG. 3 illustrates the first optical tip-tracking system 100, FIG. 4 illustrates the first optical tip-tracking system 100 including a catheter 450, and FIG. 8 illustrates the first optical tip-tracking system 100 in use, in accordance with some embodiments. FIG. 2 provides a block diagram of a second optical tip-tracking system 200 and FIG. 9 illustrates the second optical tip-tracking system 200 in use, in accordance with some embodiments.

As shown, the optical tip-tracking system 100 or 200 includes a light-emitting stylet 110, a light detector 120, and a console 130 or 230 configured to operably connect to the light-emitting stylet 110 and the light detector 120. Each optical tip-tracking system of the optical tip-tracking systems 100 and 200 also includes a display screen; however, the optical tip-tracking system 100 includes a standalone display screen 140, whereas the optical tip-tracking system 200 includes an integrated display screen 240. Each optical tip-tracking system of the optical tip-tracking systems 100 and 200 can also include a medical device 150 such as the catheter 450 of FIG. 4.

Beginning with the consoles 130 and 230, the console 130 or 230 includes memory 134 such as primary memory 136 and secondary memory 138. The primary memory 136 includes random-access memory ("RAM"). The secondary memory 138 includes non-volatile memory such as read-only memory ("ROM") including a set of instructions 139 or 239 for loading into the primary memory 136 at runtime of the console 130 or 230.

One or more processors 132 are configured to instantiate an optical tip-tracking process in accordance with the instructions 139 or 239 for optically tracking a distal-end portion of the light-emitting stylet 110 while the light-emitting stylet 110 is disposed in a vasculature of a patient, a light source such as one or more LEDs 112 is emitting light, the light detector 120 is disposed over the light-emitting stylet 110, and a plurality of photodetectors of the light detector 120 such as photodetectors 122 are detecting the light emitted from the light source of the light-emitting stylet 110. The optical tip-tracking process is configured to provide tracking information as input to a display server of the console 130 or 230 for optically tracking the distal-end portion of the light-emitting stylet 110 in a graphical user interface on the display screen 140 or 240. Optically tracking the distal-end portion of the light-emitting stylet 110 can be animated on the display screen 140 or 240 as shown on the display screen 240 of the console 230 in FIGS. 8 and 9.

FIGS. 1 and 2 provide different connection options for connecting at least the light-emitting stylet 110 and the light detector 120 to the console 130 or 230.

The left-hand side of each figure or FIGS. 1 and 2 shows a connection option ("option A") in which the light-emitting stylet 110 and the light detector 120 are independently connected to the console 130 or 230. For example, the console 130 or 230 and the light-emitting stylet 110 can be mutually configured such that the light-emitting stylet 110 directly connects to the console 130 or 230 or indirectly connects to the console 130 or 230 through an intervening multi-use cable having requisite conveying means for conveying electrical power (e.g., electrical leads), light (e.g., optical fiber), etc. Likewise, the console 130 or 230 and the light detector 120 can be mutually configured such that the light detector 120 directly connects to the console 130 or 230 or indirectly connects to the console 130 or 230 through an intervening multi-use cable.

The right-hand side of each figure of FIGS. 1 and 2 shows a connection option ("option B") in which the light-emitting stylet 110 is connected to the light detector 120 and, in turn, the light detector 120 is connected to the console 130 or 230. A cable such as the intervening multi-use cable set forth above for connecting the light detector 120 to the console 130 or 230 includes the requisite conveying means for conveying electrical power (e.g., electrical leads), light (e.g., optical fiber), etc. The foregoing connection option is useful in that the light detector 120 is multi-use equipment configured to be placed over a patient P and under a sterile drape 801 outside a sterile field as shown in FIGS. 8 and 9. The light-emitting stylet 110 is single-use equipment intended for use within the foregoing sterile field. As shown in FIG. 9, the light-emitting stylet 110 can include a drape-piercing connector 900 in a proximal-end portion thereof having a piercing element 902 configured to both pierce the sterile drape 801 and insert into a receptacle 904 of a light-detector connector extending from the light detector 120 under the sterile drape 801. So configured, the intervening multi-use cable set forth above through which the light-emitting stylet 110 can be indirectly connected to the console 130 or 230 is not needed. For examples of drape-piercing connectors for the light-emitting stylet 110 and light-detector connectors for the light-detector 120 see U.S. Pat. No. 10,231,753 and children patents or patent applications thereof, each of which patents and patent application are incorporated herein by reference.

Both connection options of FIG. 1 show the display screen 140 connected to the console 130 in the optical tip-tracking system 100. FIG. 2 does not show connection options for connecting the integrated display screen 240 to the console 230 in the optical tip-tracking system 200. This is because the integrated display screen 240 is integrated into the console 240 as shown in FIGS. 3, 4, 8, and 9.

In addition to FIGS. 1-4, FIG. 7 illustrates a side view of the light detector 120 in accordance with some embodiments.

As set forth above, the light detector 120 is configured to be placed over a patient and under a sterile drape such as the sterile drape 801 of FIGS. 8 and 9.

Figure 7:
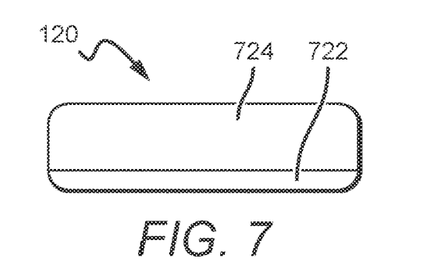
FIG. 7 illustrates a side view of a light detector of the first or second optical tip-tracking system in accordance with some embodiments.

The light detector 120 includes the photodetectors 122 disposed within the light detector 120 configured to detect the light emitted from the light source of the light-emitting stylet 110. The photodetectors 122 are arranged in an array such that the light emitted from the light source of the light-emitting stylet 110 remains detectable by at least one photodetector of the photodetectors 122 even when the light emitted from the light source of the light-emitting stylet 110 is anatomically blocked (e.g. by a rib) from another one or more photodetectors of the photodetectors 122.

The light detector 120 includes a housing having a patient-facing portion 722 of the housing configured to transmit at least a portion of the light emitted from the light source of the light-emitting stylet 110 to the photodetectors 122 disposed within the light detector 120. The housing also has a light-blocking portion 724 of the housing opposite the patient-facing portion 722 of the housing configured to block ambient light from the photodetectors 122 disposed within the light detector 120. In addition to the light-blocking portion 724 of the housing of the light detector 120, the sterile drape 801 also protects the photodetectors 122 from the ambient light while in use.

Figure 5A:
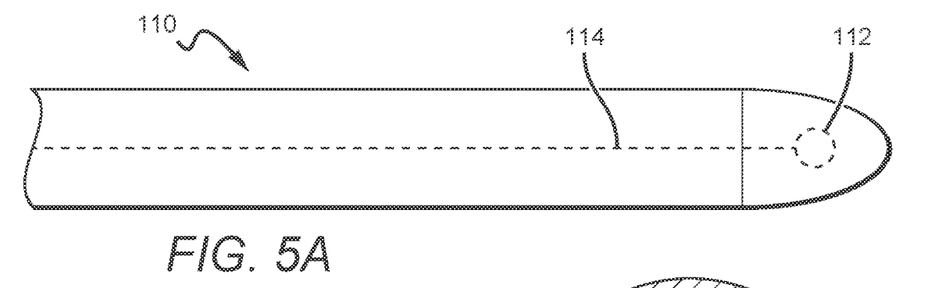
FIG. 5A illustrates a distal-end portion of a first light-emitting stylet of the first or second optical tip-tracking system in accordance with some embodiments.
Figure 5B:
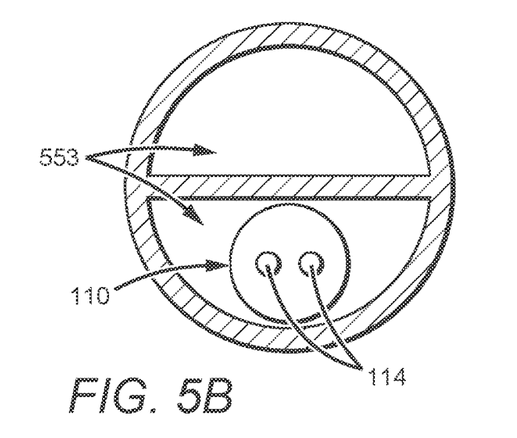
FIG. 5B illustrates a transverse cross section of the first light-emitting stylet disposed in the catheter in accordance with some embodiments.
Figure 6A:
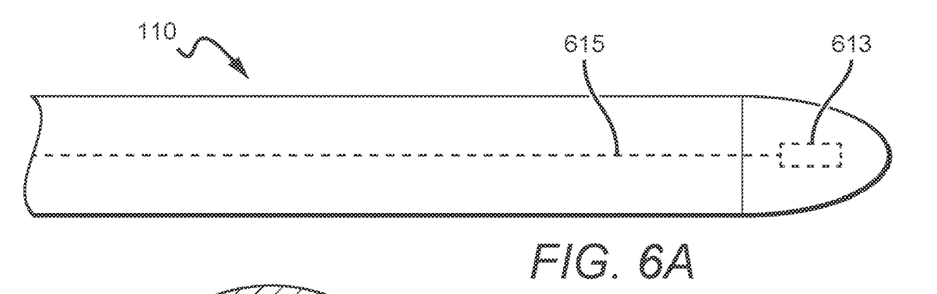
FIG. 6A illustrates a distal-end portion of a second light-emitting stylet of the first or second optical tip-tracking system in accordance with some embodiments.
Figure 6B:
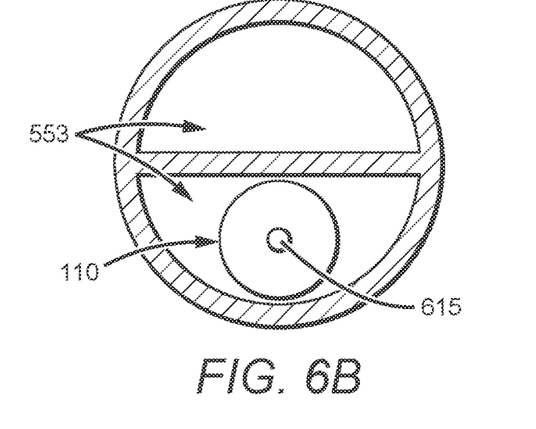
FIG. 6B illustrates a transverse cross section of the second light-emitting stylet disposed in the catheter in accordance with some embodiments.

In addition to FIGS. 1-4, FIG. 5A illustrates the distal-end portion of the light-emitting stylet 110 and FIG. 5B illustrates a transverse cross section of the light-emitting stylet 110 in accordance with some embodiments having the one-or-more LEDs 112 as the light source. FIG. 6A illustrates the distal-end portion of the light-emitting stylet 110 and FIG. 6B illustrates a transverse cross section of the light-emitting stylet 110 in accordance with some embodiments having an external light source.

As set forth in more detail below, the light-emitting stylet 110 is configured to be disposed in a lumen of a catheter.

With respect to the light-emitting stylet 110 having the one-or-more LEDs 112 as the light source, the light-emitting stylet 110 includes the one-or-more LEDs 112 in a distal-end portion (e.g., a tip) of the light-emitting stylet 110 configured to emit light. The light-emitting stylet 110 also includes at least a pair of electrical leads 114 configured to convey electrical power from the console 130 or 230 to power the one-or-more LEDs 112. The distal-end portion of the light-emitting stylet 110 can be configured to directionally emit light from the one-or-more LEDs 112 in one or more chosen directions such as straight ahead in line with the light-emitting stylet 110, radially outward such as toward an extracorporeal surface of a patient, or a combination thereof.

With respect to the light-emitting stylet 110 having the external light source, the light-emitting stylet 110 includes an optical fiber 615 configured to convey light from the external source, for example, a light within the console 130 or 230, to the distal-end portion (e.g., the tip) of the light-emitting stylet 110 to emit light. A ferrule 613 disposed over a distal-end portion of the optical fiber 615 can be configured to directionally emit light from the optical fiber 615 in one or more chosen directions such as straight ahead in line with the light-emitting stylet 110, radially outward such as toward an extracorporeal surface of a patient, or a combination thereof.

Figure 10:
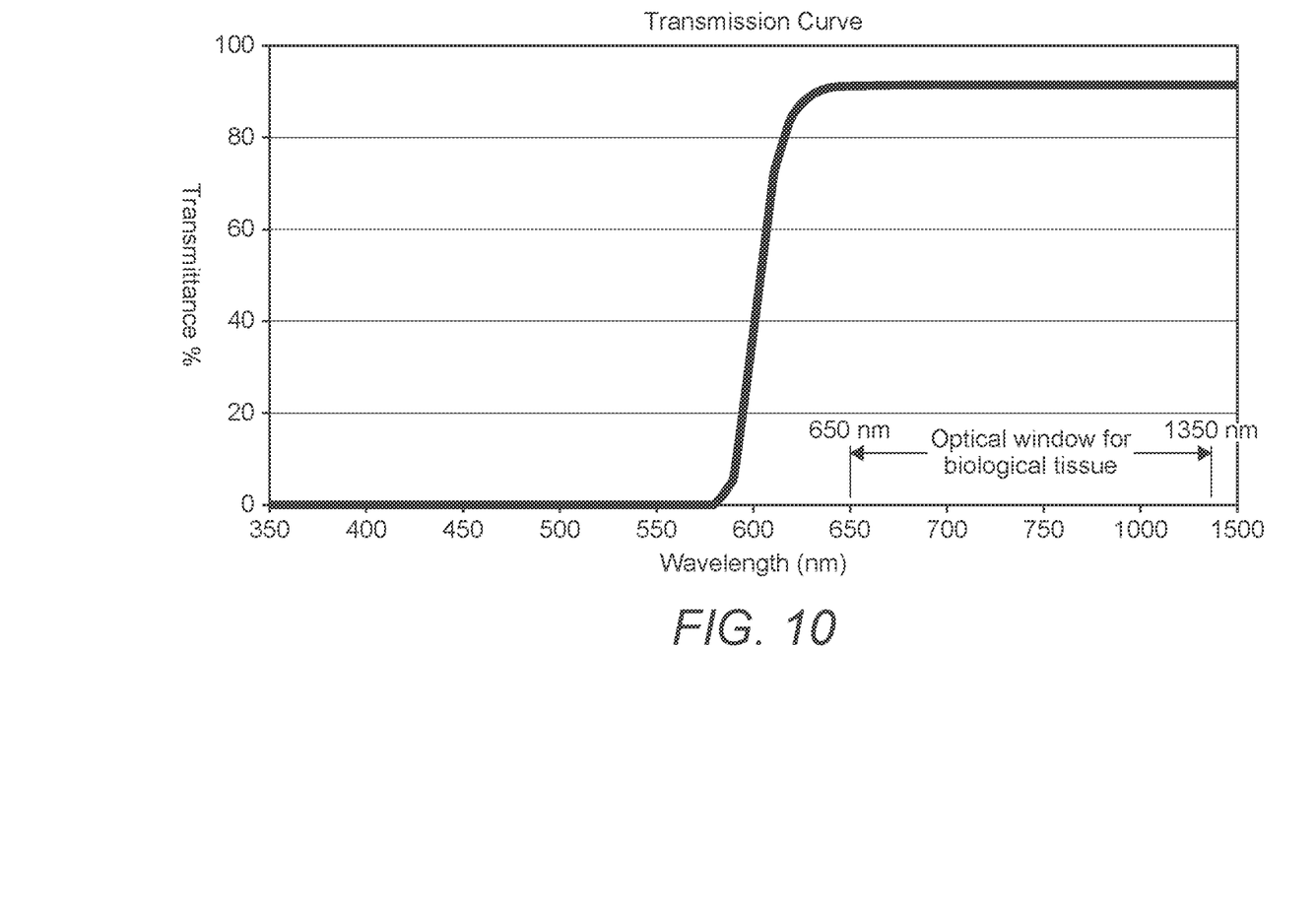
FIG. 10 provides a transmission curve for optical window for biological tissue in accordance with some embodiments.

The light emitted from the light source can have a center wavelength between about 650 nm to 1350 nm including a center wavelength between about 650 nm to 950 nm or a center wavelength between about 1100 nm to 1350 nm. The light in the foregoing ranges of wavelengths is within an optical window for biological tissue in that such light penetrates biological tissue more deeply than light outside the foregoing ranges of wavelengths. (See FIG. 10 for the optical window for biological tissue.) Each LED of the one-or-more LEDs 112 can include aluminum gallium arsenide (AlGaAs) or gallium arsenide (GaAs) as a semiconductor material. In accordance with the semiconductor material and its composition, each LED of the one-or-more LEDs 112 can be configured to emit light at or within the following wavelengths: 660 nm, 680 nm, 800-850 nm, 850-940 nm, and 940 nm.

Adverting to FIG. 4, the catheter 450 can be a peripherally inserted central catheter ("PICC"), as shown, or a central venous catheter ("CVC"). In an example of a diluminal catheter, the catheter 450 can include a catheter tube 452, a bifurcated hub 454, two extension legs 456, and two Luer connectors 458 operably connected in the foregoing order. Notwithstanding the foregoing example, the catheter 450 can alternatively be a monoluminal catheter or a multiluminal catheter including three or more lumens.

Continuing with the example of the diluminal catheter, the catheter 450 includes two lumens extending therethrough formed of adjoining lumen portions. Indeed, the catheter tube 452 includes two catheter-tube lumens 553. (See FIGS. 5B and 6B for the two catheter-tube lumens 553). The bifurcated hub 454 has two hub lumens correspondingly fluidly connected to the two catheter-tube lumens 553. Each extension leg of the two extension legs 456 has an extension-leg lumen fluidly connected to a hub lumen of the two hub lumens. Either lumen extending through the catheter 450 can accommodate the light-emitting stylet 110 disposed therein.

Methods

A method of the optical tip-tracking system 100 or 200 includes a disposing step of disposing the light-emitting stylet 110 of the optical tip-tracking system 100 or 200 in a lumen of the catheter 450.

The method also includes a placing step of placing the light detector 120 of the optical tip-tracking system 100 or 200 over the patient P as shown in FIGS. 8 and 9.

The method also includes a placing step of placing the sterile drape 801 over both the patient P and the light detector 120.

As shown in FIG. 8, the method can also include a connecting step of connecting the drape-piercing connector of the light-emitting stylet 110 with the light-detector connector extending from the light detector 120. Such a connecting step includes piercing the sterile drape 801 with the piercing element of the drape-piercing connector before inserting the piercing element into the receptacle of the light-detector connector.

The method also includes an advancing step of advancing the catheter 450 from an insertion site to a destination within a vasculature of the patient P while emitting light from the light source (e.g., the one-or-more LEDs 112) and detecting the light with the photodetectors 122. The light source of the light-emitting stylet 110 should distally extends beyond a distal end of the catheter 450 while advancing the catheter 450, thereby enabling the photodetectors 122 of the light detector 120 to detect the light emitted from the light source of the light-emitting stylet 110.

When the catheter 450 is a CVC, the advancing step includes advancing the CVC with the light-emitting stylet 110 disposed therein through a right internal jugular vein, a right brachiocephalic vein, and into an SVC.

When the catheter 450 is a PICC, the advancing step includes advancing the PICC with the light-emitting stylet 110 disposed therein through a right basilic vein, a right axillary vein, a right subclavian vein, a right brachiocephalic vein, and into an SVC.

The method also includes a viewing step of viewing the display screen 140 or 240 of the optical tip-tracking system 100 or 200 while the display screen 140 or 240 graphically tracks the distal-end portion of the light-emitting stylet 110 through the vasculature of the patient P.

The method also includes a ceasing step of ceasing to advance the catheter 450 through the vasculature of the patient P after determining the distal-end portion of the light-emitting stylet 110 is located at the destination by way of the display screen 140 or 240.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An optical tip-tracking system, comprising:
   a light-emitting stylet configured to be disposed in a lumen of a catheter, the light-emitting stylet including a light source in a distal-end portion of the light-emitting stylet configured to emit light and an electrical lead configured to convey electrical power to the light source;
   a light detector configured to be placed over a patient and under a sterile drape, the light detector including a housing, wherein the housing includes a plurality of photodetectors, wherein the plurality of photodetectors are configured to detect the light emitted from the light source, wherein the light-emitting stylet includes a drape-piercing connector having a piercing element configured to pierce the sterile drape and insert into a receptacle of a light-detector connector extending from the light detector under the sterile drape;
   and a console configured to operably connect to the light-emitting stylet and the light detector, wherein the light-emitting stylet is configured to indirectly connect to the console through the light detector, the console including memory and a processor, wherein memory storing instructions that, when executed by the processor, are configured to instantiate an optical tip-tracking process for optically tracking the distal-end portion of the light-emitting stylet while, i) the light source is emitting light, wherein the light-emitting stylet is configured to be disposed in a vasculature of the patient while the light source is emitting light, ii) the light detector is disposed over the light-emitting stylet, and (iii) the plurality of photodetectors are detecting the light emitted from the light source.

2. The optical tip-tracking system of claim 1, wherein the light source is a light-emitting diode ("LED").

3. The optical tip-tracking system of claim 1, wherein the light emitted from the light source has a center wavelength between about 650 nm to 1350 nm.

4. The optical tip-tracking system of claim 1, wherein the light emitted from the light source has a center wavelength between about 650 nm to 950 nm.

5. The optical tip-tracking system of claim 1, wherein the distal-end portion of the light-emitting stylet is configured to directionally emit light in one or more chosen directions.

6. The optical tip-tracking system of claim 1, wherein the housing includes a patient-facing portion configured to transmit at least a portion of the light emitted from the light source to the plurality of photodetectors.

7. The optical tip-tracking system of claim 6, wherein the housing has a light-blocking portion opposite the patient-facing portion, wherein the light-blocking portion is configured to block ambient light from the plurality of photodetectors.

8. The optical tip-tracking system of claim 1, wherein the plurality of photodetectors are arranged in an array such that the light emitted from the light source remains detectable by at least one photodetector of the plurality of photodetectors when the light emitted from the light source is anatomically blocked from one or more photodetectors of the photodetectors.

9. The optical tip-tracking system of claim 1, wherein the optical tip-tracking process is configured to provide tracking information as input to the console, enabling generation of a graphical user interface on a display, wherein the graphical user interface enables optical tracking of the distal-end portion of the light-emitting stylet.

10. The optical tip-tracking system of claim 1, wherein the light-emitting stylet is configured to directly connect to the console.

11. The optical tip-tracking system of claim 1, wherein the light-emitting stylet is configured to indirectly connect to the console through an intervening multi-use cable.

12. An optical tip-tracking system, comprising:
    a catheter including a lumen extending through the catheter;
    a light-emitting stylet configured to be disposed in the lumen of the catheter, the light-emitting stylet including a light-emitting diode ("LED") in a distal-end portion of the light-emitting stylet configured to emit light and an electrical lead configured to convey electrical power to the LED;
    a light detector configured to be placed over a patient and under a sterile drape, the light detector including a housing, wherein the housing includes a plurality of photodetectors arranged in an array and configured to detect the light emitted from the LED, wherein the light-emitting stylet includes a drape-piercing connector having a piercing element configured to pierce the sterile drape and insert into a receptacle of a light-detector connector extending from the light detector under the sterile drape;
    and a console configured to operably connect to the light-emitting stylet and the light detector, wherein the light-emitting stylet is configured to indirectly connect to the console through the light detector, the console including memory and a processor, wherein memory storing instructions that, when executed by the processor, are configured to instantiate an optical tip-tracking process for optically tracking the distal-end portion of the light-emitting stylet on a graphical user interface on a display while the LED is emitting light, wherein the light-emitting stylet is configured to be disposed in a vasculature of the patient while the light source is emitting light, (ii) the light detector is disposed over the light-emitting stylet, and {iii) the plurality of photodetectors are detecting the light emitted from the LED.

13. An optical tip-tracking system, comprising:
a light-emitting stylet configured to be disposed in a lumen of a catheter, the light-emitting stylet including an optical fiber configured to convey light to a distal-end portion of the light-emitting stylet for emitting light therefrom, and wherein a ferrule is disposed over a distal-end portion of the optical fiber and configured to direct light in one or more directions;
a light detector configured to be placed over a patient and under a sterile drape, the light detector including a plurality of photodetectors configured to detect the light emitted from the light-emitting stylet, wherein, the light-emitting stylet includes a drape-piercing connector having a piercing element configured to pierce the sterile drape and insert into a receptacle of a light-detector connector extending from the light detector under the sterile drape;
and a console configured to operably connect to the light-emitting stylet and the light detector, wherein the light-emitting stylet is configured to indirectly connect to the console through the light detector, the console including:
a light source for the light-emitting stylet;
and memory and a processor, wherein memory storing instructions that, when executed by the processor, are configured to instantiate an optical tip-tracking process for optically tracking the distal-end portion of the light-emitting stylet while the light-emitting stylet is disposed in a vasculature of the patient, the light-emitting stylet is emitting light, the light detector is disposed over the light-emitting stylet, and the plurality of photodetectors are detecting the light emitted from the light-emitting stylet.

14. A method of an optical tip-tracking system, comprising:
disposing a light-emitting stylet of the optical tip-tracking system in a lumen of a catheter, the light-emitting stylet including a light source in a distal-end portion of the light-emitting stylet and configured to emit light and an electrical lead configured to convey electrical power to the light source;
placing a light detector of the optical tip-tracking system over a patient, the light detector including a housing, wherein the housing includes a plurality of photodetectors, and wherein the plurality of photodetectors is configured to detect light emitted from the light source;
placing a sterile drape over both the patient and the light detector;
connecting a drape-piercing connector of the light-emitting stylet with a light-detector connector extending from the light detector, the connecting including piercing the sterile drape with a piercing element of the drape-piercing connector before inserting the piercing element into a receptacle of the light-detector connector;
advancing the catheter from an insertion site toward a destination site while emitting the light from the light source and detecting the light with the plurality of photodetectors, wherein the catheter is configured to be advanced through a vasculature of the patient; and viewing a display screen of the optical tip-tracking system while the display screen graphically tracks the distal-end portion of the light-emitting stylet through the vasculature of the patient.

15. The method of claim 14, wherein anoptical fiber of the light-emitting stylet distally extends beyond a distal end of the catheter while advancing the catheter, thereby enabling the plurality of photodetectors of the light detector to detect the light emitted from the optical fiber.

16. The method of claim 14, wherein the catheter is a central venous catheter ("CVC"), the advancing including advancing the CVC with the light-emitting stylet disposed therein through a right internal jugular vein, a right brachiocephalic vein, and into a superior vena cava ("SVC").

17. The method of claim 14, wherein the catheter is a peripherally inserted central catheter ("PICC"), the advancing including advancing the PICC with the light-emitting stylet disposed therein through a right basilic vein, a right axillary vein, a right subclavian vein, a right brachiocephalic vein, and into a superior vena cava ("SVC").

18. The method of claim 14, further comprising ceasing to advance the catheter through the vasculature of the patient after determining the distal-end portion of the light-emitting stylet is located at the destination site by way of the display screen.

* * * * *